United States Patent [19]

Ondetti et al.

[11] 4,154,942
[45] May 15, 1979

[54] CERTAIN TETRAHYDROPYRIDINE-2-CARBOXYLIC ACIDS AND PYRROLINE-2-CARBOXYLIC ACIDS AND DERIVATIVES THEREOF

[75] Inventors: Miguel A. Ondetti, Princeton; Sesesa I. Natarajan, Lawrenceville, both of N.J.

[73] Assignee: E. R. Squibb & Sons, Inc., Princeton, N.J.

[21] Appl. No.: 933,950

[22] Filed: Aug. 15, 1978

Related U.S. Application Data

[62] Division of Ser. No. 878,144, Feb. 15, 1978.

[51] Int. Cl.$^2$ ............... C07D 213/55; C07D 207/22
[52] U.S. Cl. ............... 546/326; 260/326.46; 424/266; 424/274
[58] Field of Search ............... 546/314, 326; 260/326.46

[56] References Cited

U.S. PATENT DOCUMENTS

| | | | |
|---|---|---|---|
| 3,531,490 | 9/1970 | Friedman et al. | 260/294.8 G |
| 3,917,815 | 11/1975 | Kalopisis et al. | 260/294.8 G |
| 4,046,889 | 9/1977 | Ondetti et al. | 424/244 |
| 4,066,658 | 1/1978 | Felix | 260/326.2 |

*Primary Examiner*—Alan L. Rotman
*Attorney, Agent, or Firm*—Lawrence S. Levinson; Merle J. Smith

[57] ABSTRACT

New compounds which have the general formula

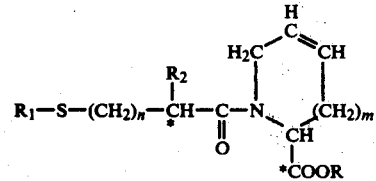

are useful as hypotensive agents.

11 Claims, No Drawings

CERTAIN TETRAHYDROPYRIDINE-2-CARBOXYLIC ACIDS AND PYRROLINE-2-CARBOXYLIC ACIDS AND DERIVATIVES THEREOF

This is a division of application Ser. No. 878,144, filed Feb. 15, 1978.

SUMMARY OF THE INVENTION

This invention relates to new compounds which have the general formula

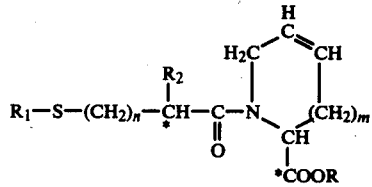

wherein
R and $R_2$ each is hydrogen or lower alkyl;
$R_1$ is hydrogen, lower alkanoyl or

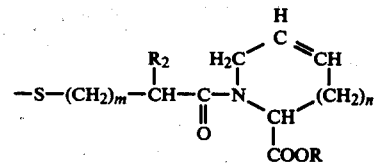

m and n each is 0 or 1.

The asterisks indicate asymmetric carbon atoms. The carbon in the acyclic side chain is asymmetric when $R_2$ is other than hydrogen.

DETAILED DESCRIPTION OF THE INVENTION

This invention relates to derivatives of 3,4-dehydroproline and 4,5-dehydropipecolic acid having formula I above.

Preferred are those compounds of formula I wherein R and $R_2$ each is hydrogen or lower alkyl, especially hydrogen or methyl; $R_1$ is hydrogen or lower alkanoyl, especially hydrogen or acetyl; m is 0 or 1, especially 0; and n is 0 or 1, especially 1.

The L-configuration for the cyclic imino acid is especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. the $C_1$–$C_4$ members, especially $C_1$ and $C_2$ members are preferred.

The lower alkanoyl groups are those having the acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

The products of formula I can be produced by various methods of synthesis.

In general, these compounds can be synthesized by coupling the acid of the formula

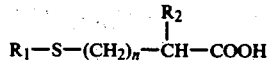  (II)

to the cyclic imino acid of the formula

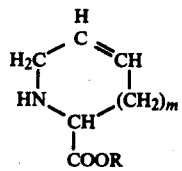

by any method which can be used to form amide bonds. See, for example, "Methoden der Organischen Chemie" (Houben-Weyl) part 1, p. 736 et seq., part II, p. 1 et seq. (1974). According to one method, an acid or ester of formula III is coupled with a haloalkanoic acid of the formula

  (IV)

wherein X is a halogen, preferably chlorine or bromine, by one of the known procedures in which the acid IV is activated, prior to reaction with the acid III, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

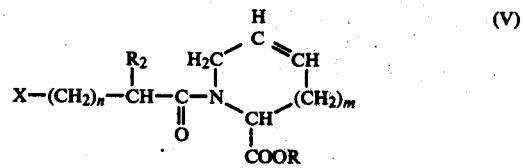  (V)

This product is subjected to a displacement reaction with the anion of a thioacid of the formula $$R_3-CO-SH \qquad (VI)$$

wherein $R_3$ is lower alkyl; yielding a product of the formula

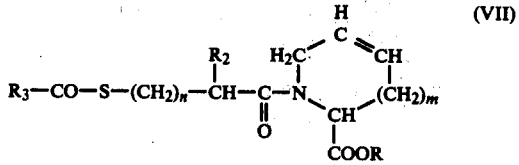  (VII)

which can then be converted to the product

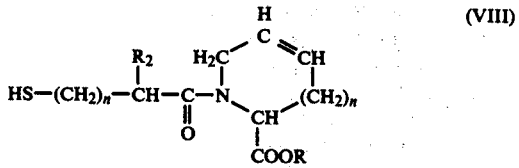  (VIII)

by ammonolysis. When OR is an ester group (i.e., R is lower alkyl), the ester group can be removed by conventional procedures. For example, when R is tert-butoxy or tert-amyloxy, treatment of the ester of formula VII or VIII with trifluoroacetic acid and anisole will give the corresponding free acid. When other alkoxy groups are present alkaline hydrolysis of the compound of formula VII or formula VIII will yield the free acid.

When an acid of formula III is used as starting material, or the final product is obtained as the free carboxylic acid, this acid can be converted to its ester, for example, by esterification with a diazoalkane, like diazomethane, 1-alkyl-3-p-tolyl-triazene, like 1-n-butyl-3-p-tolyltriazene or the like.

According to another variation, an ester, preferably the methyl or t-butyl ester, of formula III, in an anhydrous medium such as dichloromethane, tetrahydrofuran, dioxane or the like, is treated with an acylthioalkanoic acid of the formula

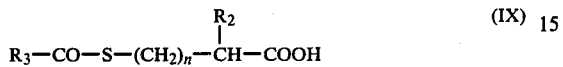

wherein $R_3$ is lower alkyl, in the presence of dicyclohexylcarbodiimide, N,N'-carbonylbisimidazole, ethoxyacetylene, diphenylphosphoryl azide or similar coupling agents at a temperature in the range of about 0° to 10° C. The ester group can then be removed, for example, by treatment with trifluoroacetic acid and anisole at about room temperature to yield the free acid (R=H).

Alternatively, an ester of formula III (e.g., R is lower alkyl, especially, t-bytyl) can be made to react with a thiolactone, e.g. β-propiothiolactone, α-methyl-β-propiothiolactone or the like in an anhydrous solvent like tetrahydrofuran, dioxane, methylene chloride or the like at about 0° C. to about room temperature. The ester group can be removed with anisole and trifluoroacetic acid as described above.

Compounds of formula I wherein $R_1$ is

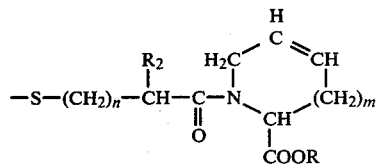

are synthesized by direct oxidation of a compound of formula I in which $R_1$ is H, e.g., with iodine, to obtain the symmetrical bis compound.

Products of formula I have one asymmetric carbon and two if $R_2$ is other than hydrogen. These carbon atoms are indicated by an asterisk in formula I. The compounds accordingly exist in stereoisomeric forms or in racemic mixtures thereof.

All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine, salts with amino acids like arginine, lysine and the like. The non-toxic, physiologically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid, and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention are useful as hypotensive agents. They inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present which has been implicated as the causative agent in various forms of hypertension in various mammalian species, e.g., rats and dogs. The compounds of this invention intervene in the angiotensinogen → (renin) → angiotensin I → (ACE) → angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavour, etc., in a unit dosage form as called for by accepted pharmaceutical practice. The amount of active substance in these compositions or preparations is such that a suitable dosage in the range indicated is obtained.

The following examples are illustrative of the invention and constitute especially preferred embodiments All temperatures are in degrees Celsius.

EXAMPLE 1

1-(3-Acetylthiopropanoyl)-DL-3,4-dehydroproline methyl ester

DL-3,4-dehydroproline methyl ester (3.75 g.) is dissolved in dichloromethane (40 ml.) and the solution is chilled in an ice-water bath. A solution of dicyclohexylcarbodiimide (6.18 g.) in dichloromethane (21 ml.) is added followed immediately by 3-acetylthiopropanic acid (4.45 g.). After fifteen minutes stirring in the ice-water bath and sixteen hours at room temperature, the precipitate is filtered off and the filtrate is concentrated to dryness in vacuo. The residue is dissolved in ethyl acetate and washed neutral. The organic layer is dried over magnesium sulfate and concentrated to dryness to yield 1-(3-acetylthiopropanoyl)-DL-3,4-dehydroproline methyl ester.

EXAMPLE 2

1-(3-Mercaptopropanoyl)-DL-3,4-dehydroproline 1-(3-Acetylthiopropanoyl)-DL-3,4-dehydroproline methyl ester (2.5 g.) is dissolved in a mixture of methanol (10 ml.) and normal sodium hydroxide (20 ml.). The mixture is stirred at room temperature under a blanket of nitrogen for two hours, diluted with water and extracted with ethyl acetate. The aqueous layer is acidified and extracted with ethyl acetate. The organic layer is dried over magnesium sulfate and concentrated to dryness to yield 1-(3-mercaptopropanoyl)-DL-3,4-dehydroproline.

EXAMPLE 3

1-(3-Acetylthiopropanoyl)-DL-3,4-dehydroproline

3-Acetylthiopropanoyl chloride (5 g.) and 2N sodium hydroxide (15 ml.) are added to a solution of DL-3,4-dehydroproline (3.4 g.) in normal sodium hydroxide (30 ml.) chilled in an ice-water bath. After three hours stirring at room temperature, the mixture is extracted with ether, the aqueous phase is acidified and extracted with ethyl acetate. The organic layer is dried over magnesium sulfate and evaporated to dryness to yield 1-(3-acetylthiopropanoyl)-DL-3,4-dehydroproline.

EXAMPLE 4

2-Ethyl-3-acetylthiopropanoic acid

Thiolacetic acid (6.61 g.), ethyl acrylic acid (6.25 g.) and a few crystals of 2,2'-azobis-(2-methylpropionitrile) are refluxed for four hours and the mixture is then allowed to stand at room temperature for forty-eight hours. The reaction mixture is concentrated to dryness and the residue reevaporated twice from toluene to yield 7.88 g. of 2-ethyl-3-acetylthiopropanoic acid.

EXAMPLE 5

2-Ethyl-3-acetylthiopropanoyl chloride

2-Ethyl-3-acetylthiopropanoic acid (7.88 g.) is dissolved in thionyl chloride (6.14 g.) and the solution is stirred at room temperature for eighteen hours. Distillation affords 2-ethyl-3-acetylthiopropanoyl chloride as a clear yellow oil, yield 4.8 g., b.p. 50°–60° (0.04 mm Hg.).

EXAMPLE 6

1-(3-Acetylthio-2-ethylpropanoyl)-L-3,4-dehydroproline

L-3,4-dehydroproline (3.4 g.) is dissolved in normal sodium hydroxide (30 ml.) and the solution is chilled in an ice-water bath. 3-Acetylthio-2-ethylpropanoyl chloride (5.84 g.) and 2 normal sodium hydroxide (15 ml.) are added and the solution is stirred at room temperature for three hours. The mixture is extracted with ether, acidified and extracted with ethyl acetate. The organic phase is dried over magnesium sulfate and evaporated to dryness to yield 1-(3-acetylthio-2-ethylpropanoyl)-L-3,4-dehydroproline.

EXAMPLE 7

1-(2-Ethyl-3-mercaptopropanoyl)-L-3,4-dehydroproline 1-(3-Acetylthio-2-ethylpropanoyl)-L-3,4-dehydroproline (3 g.) is dissolved in a mixture of water (10 ml.) and concentrated ammonia (10 ml.) under a blanket of nitrogen. After twenty-five minutes, the reaction mixture is acidified and extracted with ethyl acetate. The organic layer is dried over magnesium sulfate and evaporated to dryness to yield 1-(2-ethyl-3-mercaptopropanoyl)-L-3,4-dehydroproline.

EXAMPLE 8

1-(2-Acetylthiopropanoyld)-L-3,4-dehydroproline

L-3,4-dehydroproline (5.65 g.) is dissolved magnesium N aqueous sodium hydroxide (50 ml.) and the solution is chilled in an ice-water bath with stirring. 2N Sodium hydroxide (25 ml.) and 2-bromopropanoyl chloride (8.57 g.) are added. The mixture is stirred at room temperature for one hour. A mixture of thioacetic acid (4.18 g.) and potassium carbonate (4.8 g.) in water (50 ml.) is added and the mixture is stirred at room temperature for eighteen hours. After acidification, the mixture is extracted with ethyl acetate. The organic layer is dried over magnesum sulfate and concentrated to dryness in vacuo to yield 1-(2-acetylthiopropanoyl)-L-3,4-dehydroproline.

EXAMPLE 9

1-(2-Mercaptopropanoyl)-L-3,4-dehydroproline

By substituting 1-(2-acetylthiopropanoyl)-L-3,4-dehydroproline for the 1-(3-acetylthio-2-ethylpropanoyl)-L-3,4-dehydroproline in the procedure of Example 7, 1-(2-mercaptopropanoyl)-L-3,4-dehydroproline is obtained.

EXAMPLE 10

1-(3-Acetylthio-2-methylpropanoyl)-DL-4,5-dehydropiperidine-2-carboxylic acid

3-Acetylthio-2-methylpropanoyl chloride (5.4 g.) and 2N sodium hydroxide (15 ml.) are added to a solution of DL-4,5-dehydropiperidine-2-carboxylic acid (4 g.) in normal sodium hydroxide (30 ml.), chilled in an ice-water bath. After three hours stirring at room temperature, the mixture is extracted with ether, acidified and extracted with ethyl acetate. The organic layer is dried over magnesium sulfate, and concentrated to dryness to yield 1-(3-acetylthio-2-methylpropanoyl)-DL-4,5-dehydropiperidine-2-carboxylic acid.

EXAMPLE 11

1-(3-Mercapto-2-methylpropanoyl)-DL-4,5-dehydropiperidine-2-carboxylic acid

By substituting 1-(3-acetylthio-2-methylpropanoyl)-DL-4,5-dehydropiperidine-2-carboxylic acid for the 1-(3-acetylthio-2-ethylpropanoyl)-L-3,4-dehydroproline in the procedure of Example 7, 1-(3-mercapto-2-methylpropanoyl)-DL-4,5-dehydropiperidine-2-carboxylic acid is obtained.

EXAMPLE 12

1-(3-Mercapto-2-ethylpropanoyl)-DL-4,5-dehydropiperidine-2-carboxylic acid

By substituting DL-4,5-dehydropiperidine-2-carboxylic -carboxylic acid for L-3,4-dehydroproline in the procedure of Example 6, and the submitting the product to the procedure of Example 7, 1-(3-mercapto-2-ethylpropanoyl)-DL-4,5-dehydropiperidine-2-carboxylic acid is obtained.

EXAMPLE 13

1(2-Mercaptopropanoyl)-DL-4,5-dehydropiperidine-2-carboxylic acid

By substituting DL-4,5-dehydropiperidine-2-carboxylic acid for the L-3,4-dehydroproline in the procedure of Example 8 and then submitting the product to the procedure of Example 9, 1-(2-mercaptopropanoyl)-DL-4,5-dehydropiperidine-2-carboxylic acid is obtained.

EXAMPLE 14

1,1'-[Dithiobis-(2-methyl-3-propanoyl)]-bis-L-3,4-dehydroproline 1-(3-Mercapto-2-methylpropanoyl)-L-3,4-dehydroproline (1 g.) is dissolved in water and the pH is adjusted to 6.5 with N sodium hydroxide. An ethanolic solution of iodine is added dropwise while maintaining the pH between 6 and 7 by careful addition of N sodium hydroxide. When a permanent yellow color is obtained, the addition of iodine is stopped and the color discharged with sodium thiosulfate. The reaction mixture is acidified and extracted with ethyl acetate. The organic layer is dried over magnesium sulfate and evaporated to dryness to yield 1,1'-[dithiobis-(2-methyl-3-propanoyl)]-bis-L-3,4-dehydroproline.

EXAMPLE 15

1,1'-[Dithiobis-(2-methyl-3-propanoyl)]-bis-DL-4,5-dehydropiperidine-2-carboxylic acid By substituting 1-(3-mercapto-2-methylpropanoyl)-DL-4,5-dehydropiperidine-2-carboxylic acid for the 1-(3-mercapto-2-methylpropanoyl)-L-3,4-dehydroproline in the procedure of Example 14, 1,1'-[dithiobis-(2-methyl-3-propanoyl)-]-bis-DL-4,5-dehydropiperidine-2-carboxylic acid is obtained.

EXAMPLE 16

1-(3-Mercapto-2-methylpropanoyl)-L-3,4-dehydroproline

By substituting L-3,4-dehydroproline for the 4,5-dehydropiperidine-2-carboxylic acid in the procedure of Example 10, and then submitting the product to the procedure of Example 7, 1-(3-mercapto-2-methylpropanoyl)-L-3,4dehydroproline is obtained.

EXAMPLE 17

1-(3-Mercapto-2-methylpropanoyl)-L-3,4-dehydroproline, sodium salt

A solution of 1-(3-mercapto-2-methylpropanoyl)-L-3,4-dehydroproline in water is neutralized with 1N sodium hydroxide and the water is then removed by freeze-drying to yield 1-(3-mercapto-2-methylpropanoyl)-L-3,4-dehydroproline, sodium salt.

EXAMPLE 18

1-(3-Mercapto-2-methylpropanoyl)-L-3,4-dehydroproline dicyclohexylammonium salt

To a solution of 1-(3-mercapto-2-methylpropanoyl)-L-3,4-dehydroproline in ethyl acetate, an equimolar amount of dicyclohexylamine is added. The precipitate formed is isolated by centrifugation to yield 1-(3-mercapto-2-methylpropanoyl)-L-3,4-dehydroproline dicyclohexylammonium salt.

What is claimed is:

1. A compound of the formula

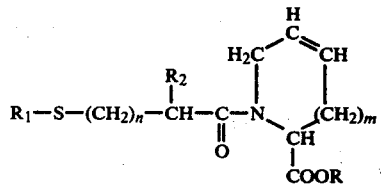

wherein
R and $R_2$ each is hydrogen or lower alkyl;
$R_1$ is lower alkanoyl
m and n each is 0 or 1;
and basic salts thereof.

2. A compound as in claim 1 wherein R and $R_2$ each is hydrogen or lower alkyl; $R_1$ is lower alkanoyl and m and n each is 0.

3. A compound as in claim 1 wherein R and $R_2$ each is hydrogen.

4. A compound as in claim 1 wherein R is hydrogen.

5. A compound as in claim 1 wherein n is 1.

6. A compound as in claim 1 wherein m is 0.

7. A compound as in claim 1 wherein m is 1.

8. A compound as in claim 4 wherein $R^1$ is acetyl.

9. A compound as in claim 3 wherein $R_1$ is acetyl; m is 0 and n is 1.

10. A compound as in claim 4 wherein $R_1$ is acetyl; $R_2$ is methyl; m is 0; and n is 0.

11. A compound as in claim 4 wherein $R_1$ is acetyl; $R_2$ is methyl; m and n each is 1.

* * * * *